(12) United States Patent
Goeldi

(10) Patent No.: US 9,526,852 B2
(45) Date of Patent: Dec. 27, 2016

(54) METHOD AND APPARATUS FOR IMPROVING FLOW AND PRESSURE ESTIMATION IN CPAP SYSTEMS

(75) Inventor: Benriah Goeldi, Lane Cove (AU)

(73) Assignee: ResMed Limited (AU)

( * ) Notice: Subject to any disclaimer, the term of this patent is extended or adjusted under 35 U.S.C. 154(b) by 1520 days.

(21) Appl. No.: 12/088,033

(22) PCT Filed: Oct. 19, 2006

(86) PCT No.: PCT/AU2006/001552
§ 371 (c)(1),
(2), (4) Date: Mar. 25, 2008

(87) PCT Pub. No.: WO2007/045036
PCT Pub. Date: Apr. 26, 2007

(65) Prior Publication Data
US 2008/0251076 A1   Oct. 16, 2008

(30) Foreign Application Priority Data
Oct. 21, 2005   (AU) ................................. 2005905830

(51) Int. Cl.
*A61M 16/00* (2006.01)

(52) U.S. Cl.
CPC ......... *A61M 16/00* (2013.01); *A61M 16/0069* (2014.02); *A61M 16/0066* (2013.01); *A61M 2016/0027* (2013.01); *A61M 2016/0036* (2013.01)

(58) Field of Classification Search
CPC ......... A61M 16/00; A61M 16/0057–16/0078; A61M 16/01

USPC ............ 128/204.18, 204.21, 204.23, 204.26
See application file for complete search history.

(56) References Cited

U.S. PATENT DOCUMENTS

| | | | |
|---|---|---|---|
| 5,299,567 A * | 4/1994 | Joye et al. | 128/204.28 |
| 5,331,995 A | 7/1994 | Westfall et al. | |
| 5,485,834 A * | 1/1996 | Joye et al. | 128/205.13 |
| 5,540,219 A | 7/1996 | Mechlenburg et al. | |
| 5,551,419 A | 9/1996 | Froehlich et al. | |
| 5,598,838 A | 2/1997 | Servidio et al. | |
| 5,609,576 A * | 3/1997 | Voss et al. | 604/67 |
| 5,704,345 A | 1/1998 | Berthon-Jones | |

(Continued)

FOREIGN PATENT DOCUMENTS

| | | |
|---|---|---|
| JP | 05-184677 | 7/1993 |
| JP | 2000516491 A | 12/2000 |

(Continued)

OTHER PUBLICATIONS

Supplementary European Search Report for Application No. 06804418.9, dated Jul. 6, 2010.

(Continued)

*Primary Examiner* — Justine Yu
*Assistant Examiner* — LaToya M Louis
(74) *Attorney, Agent, or Firm* — Lerner, David, Littenberg, Krumholz & Mentlik, LLP

(57) ABSTRACT

A CPAP apparatus in which the swing in pressure at the patient interface is adjusted by regulating the air flow from the flow generator through an air delivery conduit taking into account a pressure drop representative of the inertance of the airflow in the air delivery conduit during the increase of air flow from the flow generator.

10 Claims, 6 Drawing Sheets

(56) References Cited

U.S. PATENT DOCUMENTS

| | | |
|---|---|---|
| 6,029,665 A | 2/2000 | Berthon-Jones |
| 6,131,571 A | 10/2000 | Lampotang et al. |
| 6,142,952 A | 11/2000 | Behbehani et al. |
| 6,257,234 B1* | 7/2001 | Sun .................. 128/204.18 |
| 6,332,463 B1 | 12/2001 | Farrugia et al. |
| 6,363,933 B1 | 4/2002 | Berthon-Jones |
| 6,367,474 B1 | 4/2002 | Berthon-Jones et al. |
| 6,390,091 B1 | 5/2002 | Banner et al. |
| 6,390,092 B1* | 5/2002 | Leenhoven ........... 128/204.23 |
| 6,484,719 B1 | 11/2002 | Berthon-Jones |
| 6,502,572 B1 | 1/2003 | Berthon-Jones et al. |
| 6,532,957 B2 | 3/2003 | Berthon-Jones |
| 6,557,553 B1 | 5/2003 | Borrello |
| 6,575,163 B1 | 6/2003 | Berthon-Jones |
| 6,675,797 B1 | 1/2004 | Berthon-Jones |
| 6,688,307 B2 | 2/2004 | Berthon-Jones |
| 6,810,876 B2 | 11/2004 | Berthon-Jones |
| 6,817,361 B2 | 11/2004 | Berthon-Jones et al. |
| 6,837,242 B2* | 1/2005 | Younes ............... 128/204.22 |
| 7,128,069 B2 | 10/2006 | Farrugia et al. |
| 7,367,338 B2 | 5/2008 | Baecke et al. |
| 2005/0211248 A1* | 9/2005 | Lauk et al. ........... 128/204.23 |
| 2005/0241640 A1 | 11/2005 | Baecke et al. |

FOREIGN PATENT DOCUMENTS

| | | |
|---|---|---|
| JP | 2001-346880 | 12/2001 |
| JP | 2004508105 A | 3/2004 |
| JP | 2005-282498 | 10/2005 |
| JP | 2006-506137 | 2/2006 |
| JP | 2007524446 A | 8/2007 |
| WO | 2004/045670 A2 | 6/2004 |
| WO | 2004/112680 A2 | 12/2004 |
| WO | 2005065757 | 7/2005 |

OTHER PUBLICATIONS

European Patent Office extended Search Report for Application No. 06804418.9; Jul. 6, 2010.

* cited by examiner

METHOD AND APPARATUS FOR IMPROVING FLOW AND PRESSURE ESTIMATION IN CPAP SYSTEMS

I. FIELD OF THE INVENTION

This invention relates to a method and apparatus for delivering a supply of air at positive pressure to a patient for treating sleep disordered breathing. The invention relates to a method of improved model accuracy of the patient circuit. In one case, the invention relates to a method and apparatus which provides improved accuracy of the delivered pressures throughout a breathing cycle. Another case of the inventions application is in the use of an algorithm that determines open and closed apneas. This invention is applicable to all algorithms that must estimate the dynamic characteristics of the patient circuit.

II. BACKGROUND OF THE INVENTION

A. Summary of Positive Pressure CPAP Machines

Since the invention of nasal Continuous Positive Airway Pressure (nasal CPAP) for treatment of Obstructive Sleep Apnea (OSA) and other forms of Sleep Disordered Breathing (SDB) by Sullivan, as taught in U.S. Pat. No. 4,944,310, much effort has been directed towards improving the comfort of patients using the devices by controlling the pressure supplied to masks such as the MIRAGE® and ULTRA MIRAGE® manufactured by ResMed Limited.

Some CPAP blower devices, such as the S7™ and S8™ device by ResMed Limited, provide a supply of air at a fixed positive pressure throughout the respiratory cycle of a patient, for example, 15 cm H2O. A blower comprising an electric motor and fan can be constructed to deliver a particular pressure to a patient interface, such as a mask. When the patient breathes in with such a system, the pressure in the mask may reduce by a small amount. When the patient breathes out with such a system, the pressure in the mask may increase by a small amount. These fluctuations in mask pressure are referred to as "swing". Some blowers use feedback in a pressure controller which counterbalances the effect of patient effort on the mask pressure to reduce the swing. These devices require measuring and monitoring the mask pressure and flow and adjusting the flow generator control to maintain the mask pressure at a constant value.

B. Need for Accurate Mask Pressure Determination

What is required for each of these devices is a method to determine the pressure and flow at the patient interface. In order to accurately determine pressure and flow at a mask, one either measures them at the mask or measures them near the pressure generator and corrects for various factors, one of which is the pressure loss in a length of tubing between a pressure sensor and the mask.

i. Pressure Correction Due to Losses in the Tubing

U.S. patents that have discussed the pressure loss in tubing of CPAP devices are U.S. Pat. No. 6,817,361 entitled "Administration Of CPAP Treatment Pressure In Presence Of Apnea", U.S. Pat. No. 6,810,876 entitled "Assisted Ventilation To Match Patient Respiratory Need", U.S. Pat. No. 6,688,307 entitled "Methods And Apparatus For Determining Instantaneous Elastic Recoil And Assistance Pressure During Ventilatory Support", U.S. Pat. No. 6,675,797 entitled "Determination Of Patency Of The Airway", U.S. Pat. No. 6,575,163 entitled "Method For Calculating The Instantaneous Inspired Volume Of A Subject During Ventilatory Assistance", U.S. Pat. No. 6,532,957 entitled "Assisted Ventilation To Match Patient Respiratory Need", U.S. Pat. No. 6,502,572 entitled "Administration Of CPAP Treatment Pressure In Presence Of APNEA", U.S. Pat. No. 6,484,719 entitled "Method For Providing Ventilatory Assistance In A Spontaneously Breathing Subject", U.S. Pat. No. 6,367,474 entitled "Administration Of CPAP Treatment Pressure In Presence Of APNEA", U.S. Pat. No. 6,363,933 entitled Apparatus And Method For Controlling The Administration Of CPAP Treatment", U.S. Pat. No. 6,138,675 entitled "Determination Of The Occurrence Of An Apnea", U.S. Pat. No. 6,029,665 entitled "Determination Of Patency Of Airway", U.S. Pat. No. 5,704,345 entitled "Detection Of Apnea And Obstruction Of The Airway In The Respiratory System", and U.S. Pat. No. 5,551,419 entitled "Control For CPAP Apparatus".

These patents propose an alternative to measuring air flow and mask pressure at or near the mask by mounting flow and pressure transducers near the air pressure generator and then calculating the pressure loss along the tubing from the air pressure generator to the mask from the flow through the tubing and a knowledge of the pressure-flow characteristic of the tubing, for example, by table lookup. The pressure at the mask is then calculated by subtracting the tube pressure drop from the pressure at the pressure generator.

The pressure loss from a pressure measuring point to the mask has been calculated from the flow at the blower and the (quadratic) resistance from the measuring point to the mask according to the formula $$\Delta P = R * Q^2,$$

where $\Delta P$ is the hose pressure drop, R is the hose resistance, and Q is the flow. The mask pressure is then calculated by subtracting the hose pressure drop from the measured sensor pressure. In order to use this technique, a flow sensor is necessary, for example, a pneumotachograph and differential pressure transducer. See, e.g., U.S. Pat. No. 6,810,876 at col. 17, lines 25-50.

U.S. Pat. No. 5,551,419 also recognizes that the air pressure in the mask is a function of the pressure inside the base unit housing, the pressure generator and the pressure drop in the delivery hose. It describes the latter as a function of the flow through the hose and concludes that it is necessary to combine the pressure signal and the flow signal to produce a signal that accurately represents the pressure at the mask. See U.S. Pat. No. 5,551,419 at column 5, lines 7-12.

In order to maintain a steady mask pressure the pressure drop along the tube is added to the desired set pressure at the mask to yield the desired instantaneous pressure at the pressure generator. In some cases the controller of the pressure generator has a negative feedback input from the pressure transducer so that the desired pressure is achieved more accurately. See, e.g., U.S. Pat. No. 5,704,345 at col. 8, lines 26-55.

ii. Failure to Manage Swing

One important factor for patient comfort that must be managed is the swing. For example, for the ResMed S8 inhalation and respiratory therapy devices to ensure particular pressure stability requirements are met, the pressure difference between the inspiration and expiration phases, i.e. the swing, must not exceed 0.5 hPa ("hectopascals") to meet German MDS specifications. 1 hPa=1.04 cm H2O. The tolerance limits for inspiration and expiration fluctuations from set ventilation pressure are Ventilation pressure<10 hPa: $*p<=0.5$ hPa Ventilation pressure>=10 hPa: $*p<=1$ hPa.

The prior art techniques for determining mask pressure when the pressure sensor is not at the mask have failed to control swing consistent with these requirements. What is needed is a more accurate determination of mask pressure so that the information may be fed back to the pressure generator in order to achieve better control of swing.

iii. Failure to Predict Dynamics

The mask pressure measurement can also be used in other therapy and control related algorithms. One such algorithm is the discrimination of closed and open respiratory apneas using forced oscillations (e.g. David Bassin's "Discriminating Closed and Open Respiratory Airway Apneas by Forced Oscillation Measurements at the Flow Generator" US Provisional Application 60/823,973). This algorithm requires accurate determination of the mask pressure and flow. The hose drop model presented in the prior art fails to accurately model the dynamic characteristics of the air delivery system and as such fails to accurately model the mask pressure and flow.

III. BRIEF SUMMARY OF THE INVENTION

A. Identification of Mask Pressure Error

It has been determined that a discrepancy exists with prior art CPAP devices between the estimation of the mask pressure based upon measurements of flow and pressure at or near the location of the flow generator and the true mask pressure as accurately measured at the mask using a quality pressure transducer. This discrepancy is significant during changes in the mask pressure and flow which can be caused by patient breathing and forced oscillation.

B. Relation Between Estimated Mask Pressure and Flow Derivative

The estimated pressure loss in the air delivery system is better modeled as $$P_{drop} = K_1 Q^2 + K_2 Q + K_L \frac{dQ}{dt}$$

Where Q is the flow through the hose, $K_1$ and $K_2$ are empirically determined constants and $K_L$ is the analytically determined flow inertance.

In the case of higher frequency changes such as during forced oscillation (~4 Hz) this model models the pressure loss much more accurately.

If the pressure and flow oscillations are represented as complex numbers and we linearise about the operating point we can calculate the pressure oscillations as $$P_{drop,AC} = (2K_1 \overline{Q} + K_2 + K_L j\omega) Q_{AC}$$

Where $\overline{Q}$ is the average flow, $\omega$ is the oscillation frequency and $Q_{AC}$ is the flow oscillation represented as a complex number.

C. Relation Between Mask Pressure Swings and Flow Derivative

By careful observation and measurement it has unexpectedly been determined that the discrepancy is most significant when the derivative of flow is positive as measured at or near the location of the flow generator, and is not significant when the derivative of flow at that location is negative. Furthermore, the discrepancy ΔP, when the derivative of the flow dQ/dt is positive, has been found to be proportional to the derivative of the flow with respect to time $$\Delta P = (k) dQ/dt$$

i. Empirical Understanding of Pressure Inertance

It has also been found that the magnitude of the discrepancy is related to the physical effect of the inertia of the flowing air, which resists the acceleration caused by pressure differences. If one neglects the compression of the air and all thermodynamic effects $$\Delta P = (\rho l/A) dQ/dt.$$

where ρ is the air density, l is the length of tubing, A is the cross sectional area of the tubing and Q is the flow as a function of time. Although the air is compressible and subjected to temperature changes due to compression, the above formula gives a very good fit to the observed data for positive dQ/dt, which suggests that the effect is inertance of the air. The formula must however be considered empirical since it does not explain why there is no similar discrepancy for negative flow derivatives.

D. Aspects of the Invention

In accordance with one aspect of the invention there is provided a method and apparatus for improving the determination of mask pressure based upon the estimation of pressure at the flow generator of a CPAP device.

In accordance with another aspect of the invention there is provided a CPAP apparatus for treatment of sleep disordered breathing that reduces pressure during exhalation from a first level accurately to a second level so as to maintain the swing between preset limits.

In accordance with another aspect of the invention there is provided a method of controlling the pressure developed by the electric motor of a blower by freewheeling the motor when the pressure developed by the blower exceeds a threshold and regulating the pressure so as accurately to maintain the swing between preset limits. See U.S. Pat. No. 7,128,069 issued Oct. 31, 2006, which is incorporated herein by reference.

In another aspect of the invention, the first pressure level is determined in accordance with an automatic algorithm in which the derivative of flow is calculated at runtime, clipped to not go negative, and is bounded above by a predetermined value. The purpose of the bound is to avoid some detrimental effects of leaks in the mask.

IV. BRIEF DESCRIPTION OF THE DRAWINGS

V. DETAILED DESCRIPTION OF THE INVENTION

A. Description of a Typical Apparatus

Figure 1:
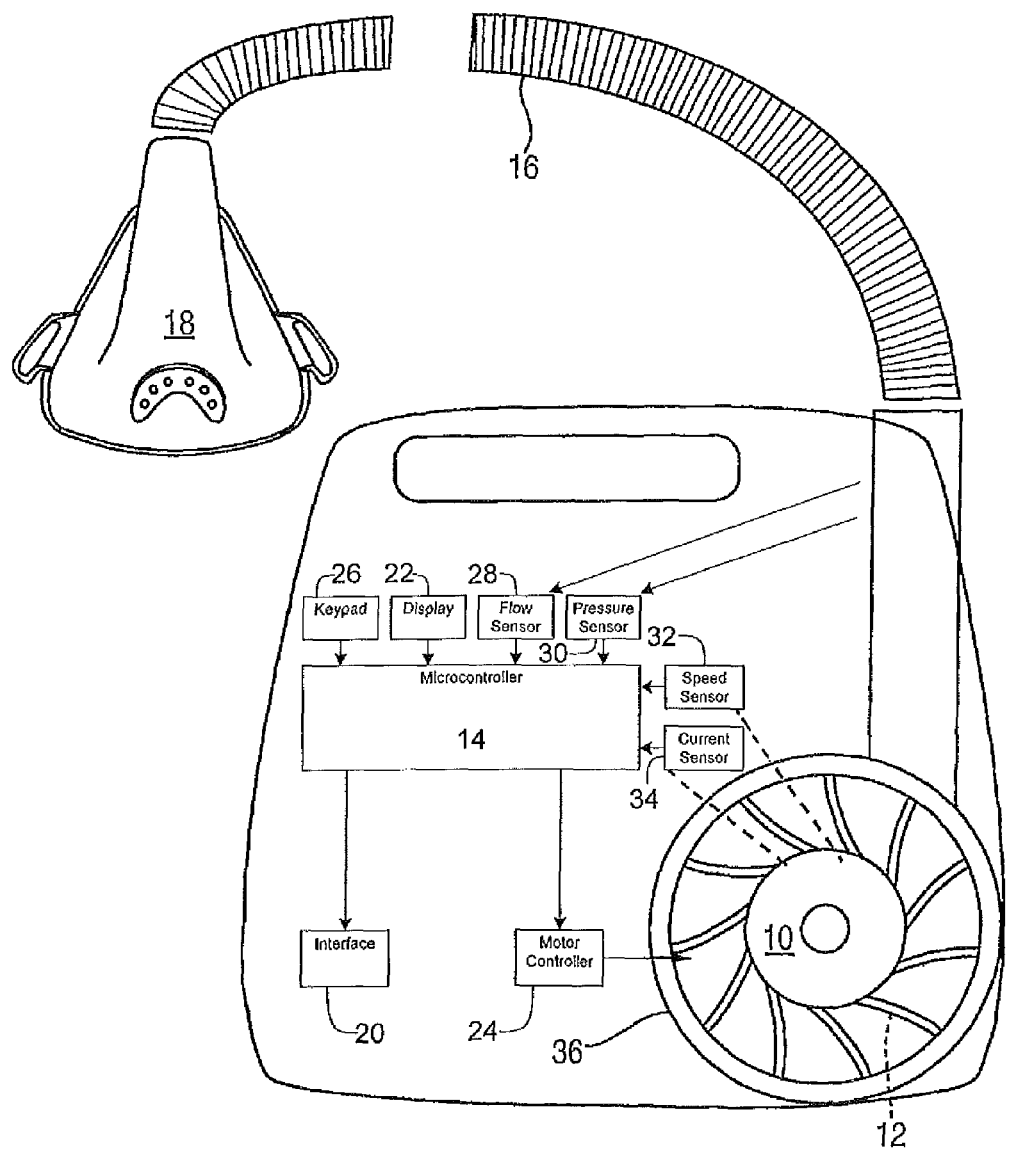
FIG. 1 shows CPAP apparatus in accordance with an embodiment of the invention.

FIG. 1 shows apparatus in accordance with an embodiment of the invention. A brushless electric motor 10 has an impeller 12 attached to it. The impeller 12 resides in a volute 36. The motor 10 is under the control of a motor controller 24 (suitable controllers include TMS320LC2402 or MC33035 ICs). The motor includes sensors 32, 34 that provide signals indicative of motor rotational speed and current, respectively. When the windings of the motor are energized, the impeller rotates. Air is drawn in through the inlet of the impeller and gains momentum. As the air passes out of the impeller and into the volute, it changes speed and develops pressure. Air passes out of the volute, past flow and pressure sensors 28, 30 (such as SMI5652-003 flow sensor and SMI5652-008 or MPX2010 pressure sensors) respectively to an air delivery conduit 16 (for example, manufactured by Smooth-bore Plastics) that is in turn connected to a patient interface 18 which in the illustrated embodiment is a nasal mask, for example, a MIRAGE® or ULTRA MIRAGE® mask manufactured by ResMed Limited. Other forms of patient interface may be used, for example, a full-face mask, nasal prongs and nasal cushions.

The flow and pressure sensors 28, 30 provide data to a microcontroller 14. Suitable microcontrollers include the HITACHI SH 7032/34 which are 32-bit RISC devices, with a clock rate of 2-20 MHz, 8 by 10 bit A-D converters and a variety of Input and Output features. The microcontroller 14 uses the Nucleus Plus Real-time Operating System (RTOS) by Accelerated Technologies Incorporated. In one form of the invention, the apparatus delivers a predetermined CPAP pressure; such a device is the S7 ELITE by ResMed Limited. In another form of the invention, the microcontroller 14 is programmed to deliver CPAP therapy in accordance with U.S. Pat. No. 5,704,345 (Berthon-Jones) which teaches a method and apparatus for detection of apnea and obstruction of the airway in the respiratory system. The contents of U.S. Pat. No. 5,704,345 are hereby incorporated by cross-reference.

The apparatus includes a display 22, for example, a 2 line by 16 character LCD or similar display device. The apparatus includes a keypad 26, such as one using backlit silicone switches. The device also includes a power supply which provides 40 W at 24V with Class II isolation manufactured by SKYNET. The apparatus may include an interface 20 to enable communication with external devices. For example, a suitable interface chip is the MAX3130/MAX3131 from MAXIM. These chips provide both IrDA and RS-232 communication.

A CPAP device such as the S7 ELITE manufactured by ResMed Limited may be adapted to incorporate our invention. Generally, the controller of the CPAP apparatus according to an embodiment of our invention is programmed to deliver a CPAP pressure in the range of 4 to 25 cm H2O. In an automatically adjusting form of the apparatus, such as the AutoSet SPIRIT and as taught in the abovementioned U.S. Pat. No. 5,704,345, the CPAP apparatus is programmed to increase the CPAP pressure to overcome or prevent partial or complete obstructions of the airway as indicated by the presence of snoring, apneas or flow flattening.

B. Mask Pressure Falls Below Flow Generator Estimation

Figure 2:
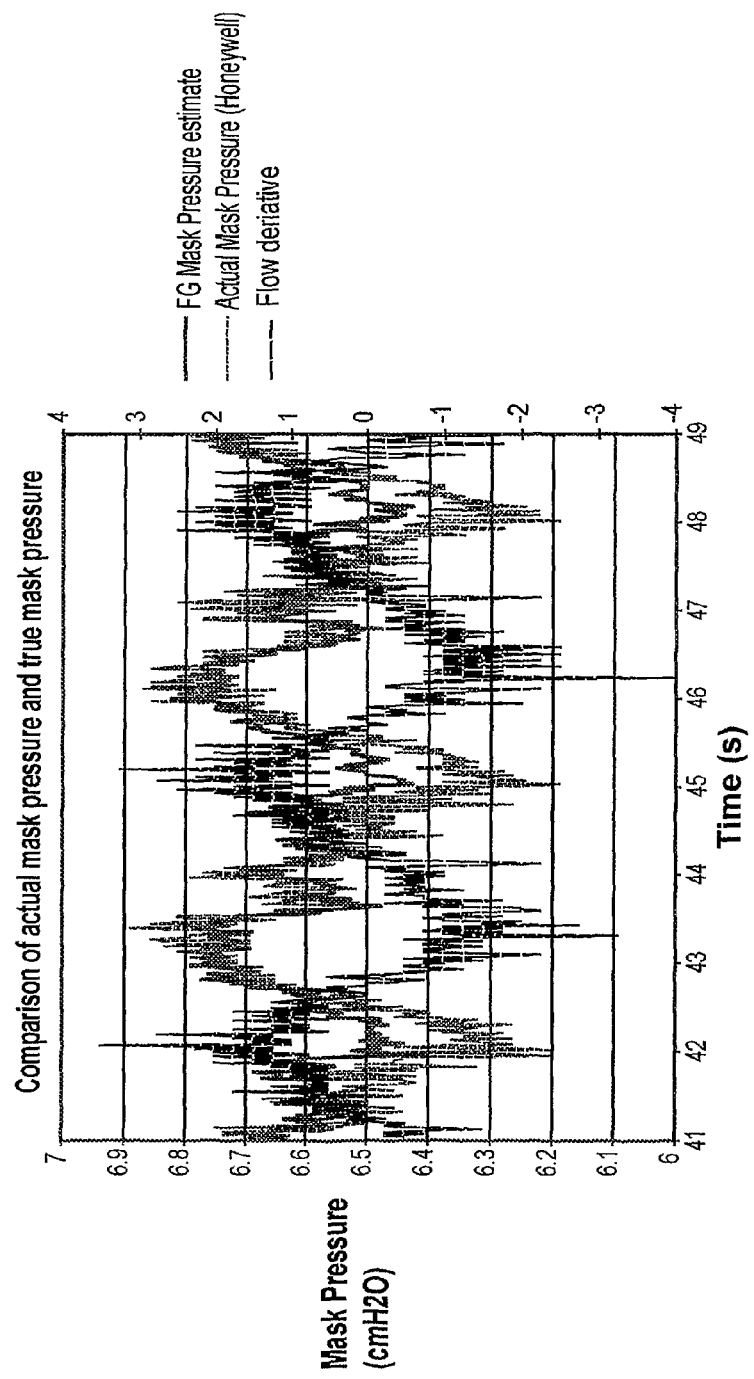
FIG. 2 shows a comparison of actual mask pressure and flow generator estimation of mask pressure before an inertance correction.

FIG. 2 shows a typical comparison of the actual mask pressure measured with a Honeywell pressure transducer in the mask as compared with the prior art estimation of the mask pressure based on flow and pressure sensors 28 and 30 of FIG. 1 located near the flow generator. As seen in the figure, the flow generator mask pressure estimate significantly exceeds the actual mask pressure in each of the time intervals where the flow derivative is positive. On the other hand, it may be seen that the measured and estimated mask pressure are substantially identical in the time intervals where the flow derivative is negative.

Figure 4:
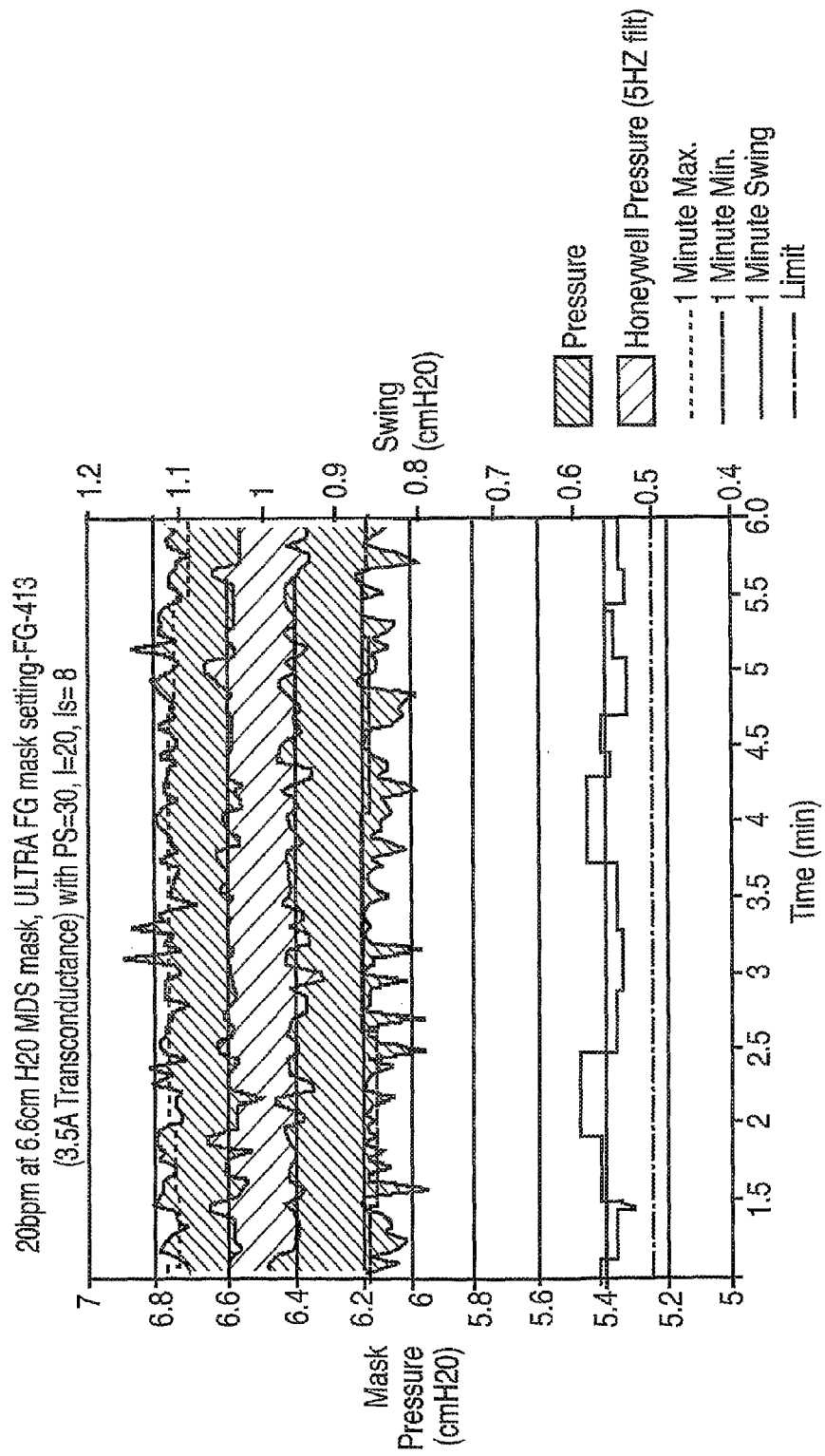
FIG. 4 shows the swing without a flow inertance correction.

FIG. 4 is based on the same data and shows the swing without a correction for flow inertance. As may be seen in the figure, the swings depicted in the curve identified as "1 minute swing" are everywhere above the 0.5 cm H2O limit.

Figure 6:
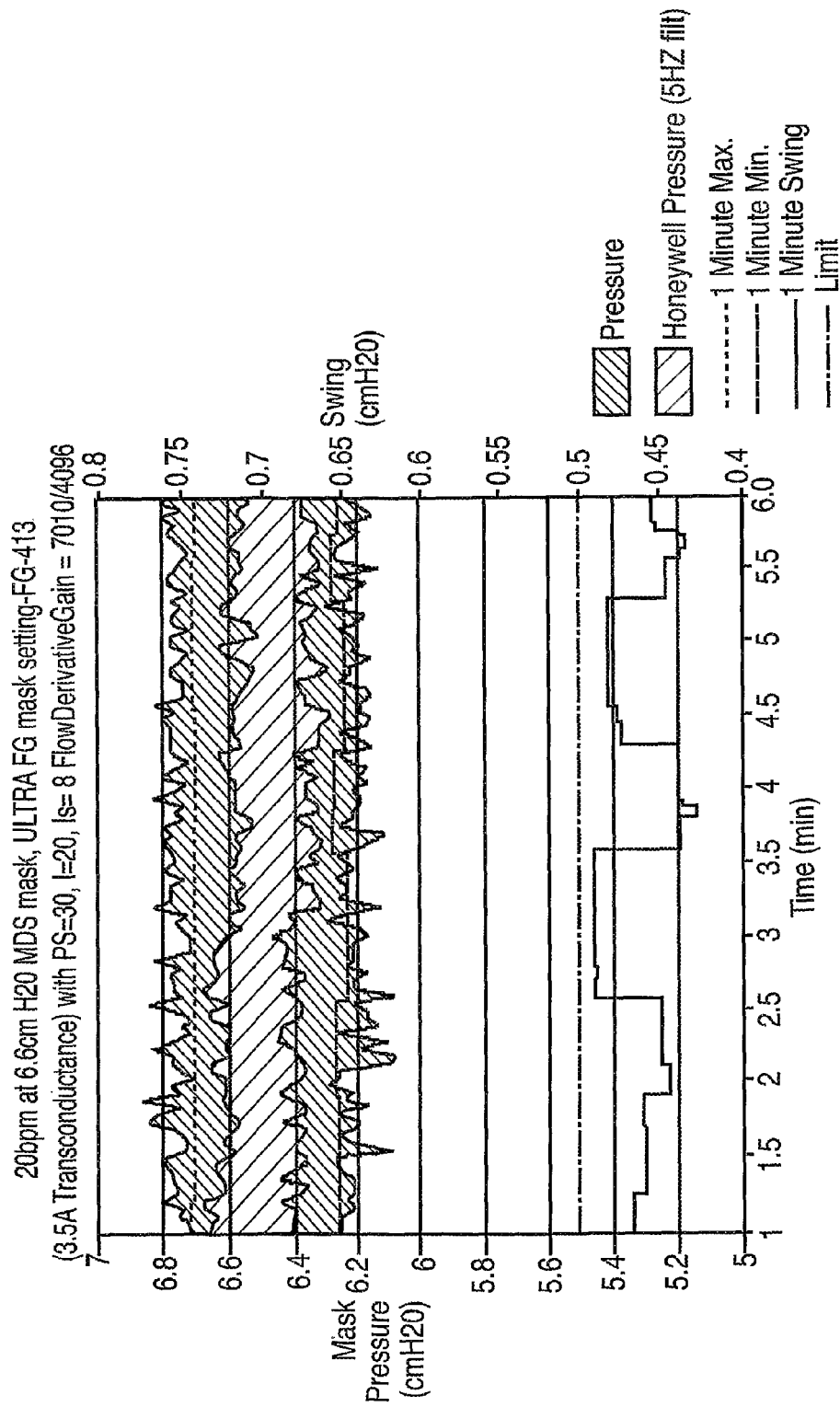
FIG. 6 shows the swing with a flow inertance correction.

FIG. 6 shows the swing with the correction for flow inertance of $$\Delta P = (\rho l/A) dQ/dt.$$

As may be seen in the figure, the swing depicted as "1 minute swing" is everywhere below the 0.5 cm H2O limit. Note that 0.5 cm H2O meets the 0.5 hPa standard for swings.

The correction for flow inertance was calculated with the following values:

$$\rho = \text{Air Density } (1.19 \text{ kg/m}^3)$$

$$l = \text{length } (2 \text{ m})$$

$$A = \text{cross section area } (d=0.019 \text{ m}), [A = \pi d^2/4].$$

These values yield $dQ/dt = 1.6$ L/s$^2$, and $\Delta P = 13.43$ Pa=1.4 mm H2O.

C. Basis for the Inertance Formula

Figure 3:
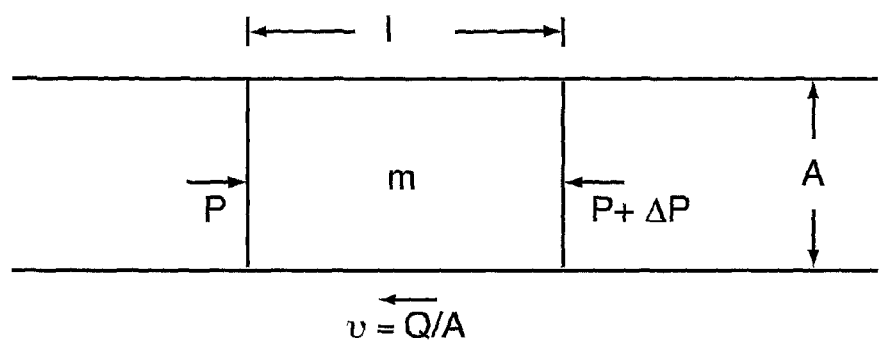
FIG. 3 shows schematically the movement of a column of air during non-constant flow.

A theoretical basis follows for the equation used to include the effect of the inertia of the air mass that is accelerated as the result of an increase in the pressure as the flow generator accelerates to increase mask pressure. The calculation is based upon the change of momentum of a mass of air flowing under the differential pressure. Consider, as shown in FIG. 3, the mass of air of density $\rho$ occupying a length l of tubing of cross section area A. It has a mass m given by density times volume:

$$m = \rho l A.$$

The mass m is flowing to the left with a velocity v that is related to the flow Q by $$v = Q/A.$$

The momentum $\Gamma$ of the mass m is mv, i.e., $$\Gamma = \rho l Q.$$

There is a pressure difference $\Delta P$ across the mass m due to the fact that the flow generator has increased the pressure behind the mass. This exerts a force $A\Delta P$ on the mass, causing it to accelerate and increase its momentum.

$$A\Delta P = d\Gamma/dt = \rho l dQ/dt$$

$$\Delta P = (\rho l/A) dQ/dt.$$

We note, from actual measurement, that this formula only gives correct values when the flow derivative is positive.

D. Implementation of the Inertance Formula

Figure 5:
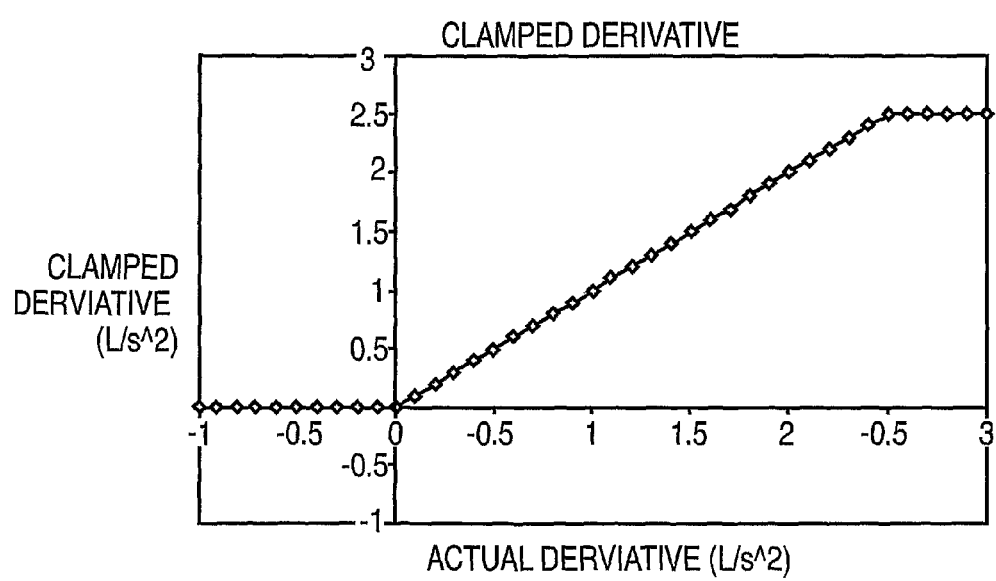
FIG. 5 shows the clamping of the calculated derivative of the flow.

The derivative of the flow is calculated as a converted value at runtime. The converted value differs from the derivative by being set to zero for negative values of the derivative and cut off at a maximum positive value of the derivative. This is referred to in FIG. 5 as clamping of the calculated derivative. FIG. 5 shows a conversion from actual values of dQ/dt, determined from subtraction of successive Q values at successive sampling times. Thus converted dQ/dt is 0 if the actual derivative is negative, converted dQ/dt is 2.5 L/s$^2$ if the actual derivative exceeds that value, and otherwise converted dQ/dt is set at the actual value. Although the application describes the clipping of the converted dQ/dt at 2.5 L/s$^2$ it is to be understood that clipping may occur at other limits. The clipping limit is a safety or protection mechanism to compensate against sudden changes in flow for example due to removal of the mask or coughing. In use the clipping may be any value above 1.

i Pressure Reduction Algorithm

In general, the sequencing takes the following steps:

(i) Upon detection of the transition from inhalation to exhalation, less energy is input to the motor and dQ/dt is negative.

(ii) When the pressure in the patient mask (or whatever interface is utilized) reaches a minimum pressure level during exhalation, more energy is input to the motor so to maintain the pressure at a level suitable for exhalation.

(iii) Upon detection of the transition from exhalation to inhalation, the motor current is altered to control the pressure, as a result of which the motor speed is increased. This causes an increase in flow, and dQ/dt is positive. dQ/dt is calculated and replaced by its converted (clamped) value.

(iv) The value attributable to the pressure in the mask is decreased by $\Delta P=(\rho l/A) \, dQ/dt$, where $\rho$ is the air density, $l$ is the length of tubing, A is the cross sectional area of the tubing, Q is the flow as a function of time, and dQ/dt is the converted (clamped) value of the flow derivative.

Although the invention has been described with reference to particular embodiments, it is to be understood that these embodiments are merely illustrative of the application of the principles of the invention. Numerous modifications may be made therein and other arrangements may be devised without departing from the spirit and scope of the invention.

We claim:

1. A method of controlling pressure in a patient interface of a CPAP apparatus, the CPAP apparatus having a flow generator, the patient interface, an air delivery conduit for delivering air from the flow generator to the patient interface, a pressure sensor for determining a pressure from the flow generator, a flow sensor for determining a flow from the flow generator, and a control mechanism that causes air to be delivered through the air delivery conduit at a desired pressure at the patient interface, the method of controlling pressure in the patient interface comprising:

sensing the pressure at the pressure sensor; sensing the flow at the flow sensor;

estimating a pressure loss in the air delivery conduit based on the sensed flow;

determining an estimated mask pressure based on the sensed pressure at the pressure sensor and the estimated pressure loss in the air delivery conduit; calculating a derivative of the flow at run time;

setting a converted derivative of flow value by converting the calculated derivative of the flow based on whether the calculated derivative of the flow is positive or negative, wherein the calculated derivative is converted based on a comparison of the calculated derivative to a threshold;

calculating a pressure discrepancy value indicative of a discrepancy of the estimated mask pressure based on the converted derivative of flow value;

determining an adjusted mask pressure at the patient interface based on the estimated mask pressure and the pressure discrepancy value; and controlling the flow generator by maintaining the adjusted mask pressure substantially equal to the desired pressure.

2. The method of claim 1, wherein the adjusted mask pressure is maintained at a value that is greater than the sensed pressure.

3. The method of claim 1, wherein in the event that the calculated derivative of flow value is negative, the converted derivative of flow value is set to a first predetermined value.

4. The method of claim 3, wherein the first predetermined value is zero.

5. The method of claim 1, wherein in the event that the calculated derivative of flow value is positive, the converted derivative of flow value is set to the calculated derivative of flow value.

6. The method of claim 1, wherein in the event that the calculated derivative of flow value is positive and greater than a second predetermined value, the converted derivative of flow value is set to the second predetermined value.

7. The method of claim 6, wherein the second predetermined value is greater than 1 liter/sec$^2$.

8. The method of claim 6, wherein the second predetermined value is approximately 2.5 liters/sec$^2$.

9. The method of claim 1, wherein the pressure discrepancy value ($\Delta P$) is calculated by $\Delta P=(\rho l/A) \, dQ/dt$, where $\rho$ is the flow's density, $l$ is the length of the air delivery conduit, A is the cross section area of the air delivery conduit, and dQ/dt is the rate of change of the flow.

10. The method of claim 1, wherein the pressure loss ($P_{drop}$) in the air delivery conduit is estimated by:

$$P_{drop}=K_1 Q^2 + K_2 Q + K_L dQ/dt;$$

where Q is the flow through the air delivery conduit, $K_1$ and $K_2$ are empirically determined constants, $K_L$ is an analytically determined flow inertance, and dQ/dt is a rate of change of the flow.

* * * * *